(12) United States Patent
Kwon et al.

(10) Patent No.: US 11,123,022 B2
(45) Date of Patent: Sep. 21, 2021

(54) BLOOD PRESSURE ESTIMATING APPARATUS AND BLOOD PRESSURE ESTIMATING METHOD

(71) Applicant: SAMSUNG ELECTRONICS CO., LTD., Suwon-si (KR)

(72) Inventors: Ui Kun Kwon, Hwaseong-si (KR); Yunseo Ku, Gwacheon-si (KR); Seung Woo Noh, Seongnam-si (KR); Chang Soon Park, Chungju-si (KR); Seung Keun Yoon, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 355 days.

(21) Appl. No.: 16/160,570

(22) Filed: Oct. 15, 2018

(65) Prior Publication Data

US 2019/0110757 A1    Apr. 18, 2019

(30) Foreign Application Priority Data

Oct. 18, 2017  (KR) .......................... 10-2017-0135399
Jul. 2, 2018   (KR) .......................... 10-2018-0076434

(51) Int. Cl.
    *A61B 5/00*    (2006.01)
    *A61B 5/029*    (2006.01)
    *A61B 5/021*    (2006.01)
    *A61B 5/0205*    (2006.01)
    (Continued)

(52) U.S. Cl.
CPC ............ *A61B 5/7278* (2013.01); *A61B 5/021* (2013.01); *A61B 5/0205* (2013.01); *A61B 5/029* (2013.01);
(Continued)

(58) Field of Classification Search
CPC ......... A61B 5/02; A61B 5/021; A61B 5/0205; A61B 5/029; A61B 5/02108;
(Continued)

(56) References Cited

U.S. PATENT DOCUMENTS 6,485,431 B1    11/2002    Campbell
8,585,605 B2    11/2013    Sola I Caros et al.
(Continued)

FOREIGN PATENT DOCUMENTS

EP        0956817 A1 * 11/1999 ......... A61B 5/02125
KR     10-0585848 B1   6/2006
(Continued)

OTHER PUBLICATIONS

Communication dated Mar. 28, 2019, issued by the European Patent Office in counterpart European Application No. 18200641.1.
(Continued)

*Primary Examiner* — Eric F Winakur
*Assistant Examiner* — Alice Ling Zou
(74) *Attorney, Agent, or Firm* — Sughrue Mion, PLLC

(57) ABSTRACT

A blood pressure estimating apparatus includes a sensor configured to obtain a bio-signal of an object; and a processor configured to extract a first cardiovascular feature and a second cardiovascular feature based on the bio-signal, and estimate blood pressure based on a first changing tendency of the first cardiovascular feature from a first reference level and a second changing tendency of the second cardiovascular feature from a second reference level, the first changing tendency and the second changing tendency being independent from each other.

28 Claims, 14 Drawing Sheets

(51) Int. Cl.
 *A61B 5/11* (2006.01)
 *A61B 5/024* (2006.01)
 *A61B 5/02* (2006.01)
 *A61B 5/318* (2021.01)
 *A61B 5/389* (2021.01)

(52) U.S. Cl.
 CPC ...... *A61B 5/02116* (2013.01); *A61B 5/02125* (2013.01); *A61B 5/681* (2013.01); *A61B 5/02007* (2013.01); *A61B 5/02028* (2013.01); *A61B 5/02108* (2013.01); *A61B 5/02416* (2013.01); *A61B 5/1102* (2013.01); *A61B 5/318* (2021.01); *A61B 5/389* (2021.01)

(58) Field of Classification Search
 CPC ............ A61B 5/02116; A61B 5/02125; A61B 5/7278; A61B 5/02416; A61B 5/024; A61B 5/318; A61B 5/1102; A61B 5/389; A61B 5/6802; G16H 50/20
 See application file for complete search history.

(56) References Cited

U.S. PATENT DOCUMENTS

| | | | |
|---|---|---|---|
| 10,702,169 B2 * | 7/2020 | Gaurav | ............ A61B 5/02125 |
| 2008/0214942 A1 | 9/2008 | Oh et al. | |
| 2012/0259189 A1 | 10/2012 | Cohen et al. | |
| 2014/0066732 A1 | 3/2014 | Addison et al. | |
| 2014/0235979 A1 | 8/2014 | Banet et al. | |
| 2014/0249424 A1 | 9/2014 | Fan et al. | |
| 2015/0073250 A1 | 3/2015 | Goor et al. | |
| 2015/0230774 A1 | 8/2015 | Thai | |
| 2016/0081563 A1 | 3/2016 | Wiard et al. | |
| 2016/0270668 A1 | 9/2016 | Gil | |
| 2016/0302735 A1 * | 10/2016 | Noguchi | ................ A61B 5/746 |
| 2016/0317043 A1 | 11/2016 | Campo et al. | |
| 2017/0112395 A1 | 4/2017 | Kim et al. | |

FOREIGN PATENT DOCUMENTS

| | | | |
|---|---|---|---|
| KR | 10-1231421 B1 | 2/2013 | |
| KR | 10-1503604 B1 | 3/2015 | |
| WO | WO-2006100676 A2 * | 9/2006 | ......... A61B 5/02125 |

OTHER PUBLICATIONS

S. Sun et al., "Systolic blood pressure estimation using PPG and ECG during physical exercise", Physical Measurement, vol. 37, No. 12, Institute of Physics and Engineering in Medicine, XP020310984, Bristol, GB, Nov. 14, 2016, pp. 2154-2169.

* cited by examiner

FIG. 5B

| No. | CANDIDATE OF CO FEATURE | CANDIDATE OF TPR FEATURE |
|---|---|---|
| 1 | HR | $1/(T3-T1)$ |
| 2 | PPGarea | $1/(T3-Tsys)$ |
| 3 | P3/Pmax | $1/(T3-Tmax)$ |
| 4 | P3/Psys | $1/(T2-T1)$ |
| 5 | Pmax/PPGarea | P2/P1 |
| 6 | 1/PPGdur | P3/Pmax |
| 7 |  | P3/P1 |
| 8 |  | PPG area |

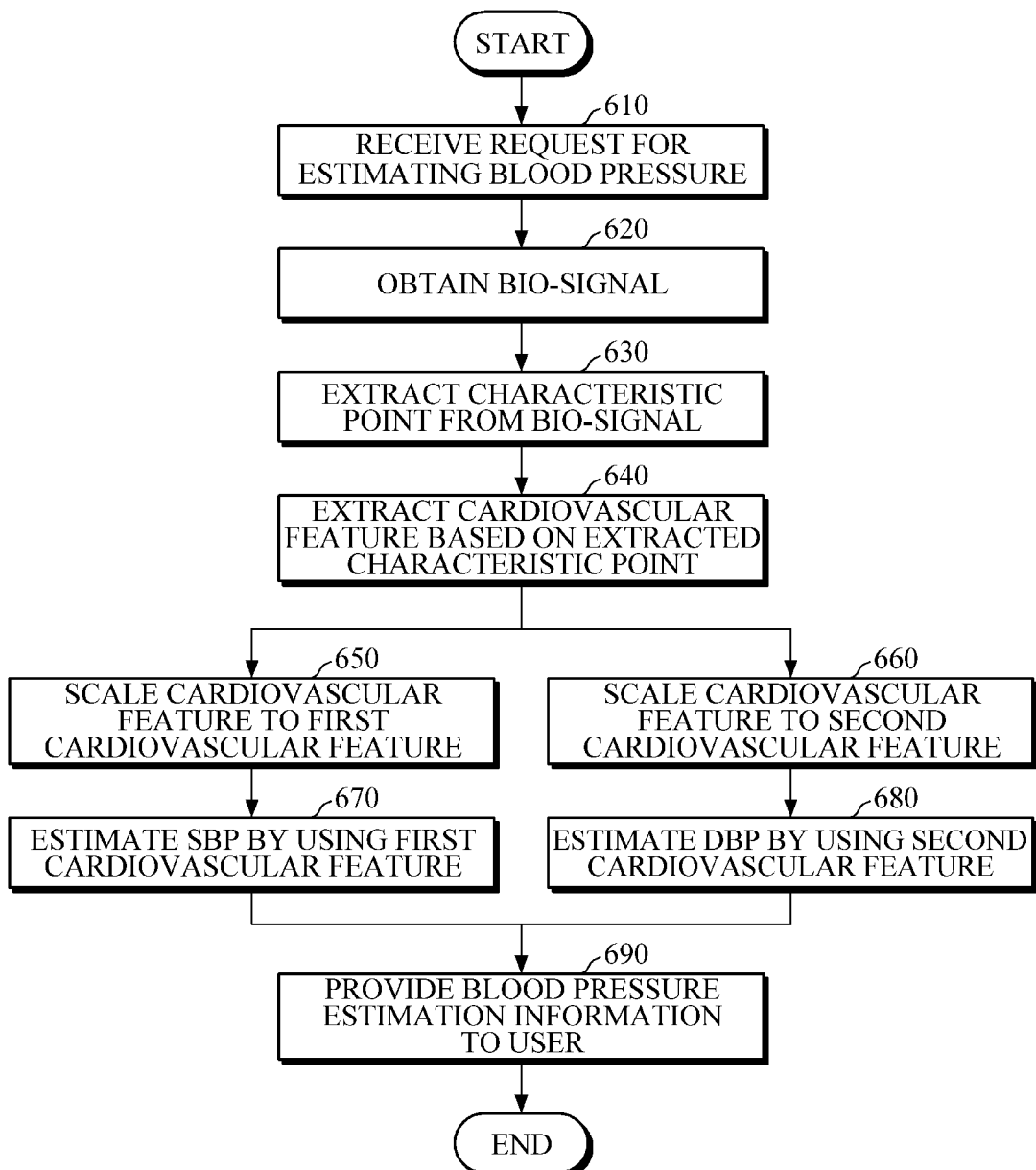

BLOOD PRESSURE ESTIMATING APPARATUS AND BLOOD PRESSURE ESTIMATING METHOD

CROSS-REFERENCE TO RELATED APPLICATION(S)

This application claims priority from Korean Patent Application No. 10-2017-0135399, filed on Oct. 18, 2017, and Korean Patent Application No. 10-2018-0076434, filed on Jul. 2, 2018 in the Korean Intellectual Property Office, the disclosures of which are incorporated herein by reference in their entireties.

BACKGROUND

1. Field

Apparatuses and methods consistent with exemplary embodiments relate to a blood pressure estimating apparatus and a blood pressure estimating method, and more particularly, to technology for independently estimating systolic blood pressure (SBP) and diastolic blood pressure (DBP) in a non-invasive manner.

2. Description of the Related Art

With the aging population, increased medical costs, and a lack of medical personnel for specialized medical services, research is being actively conducted on information technology (IT)-medical convergence technologies, in which IT technology and medical technology are combined. Particularly, monitoring of a health condition of a human body may not be limited to places such as hospitals, but is expanded by mobile healthcare fields that may monitor a user's health condition anywhere (e.g., at home or office on in transit from one place to another place) and anytime in daily life. Some examples of bio-signals, which indicate the health condition of individuals, may include an electrocardiography (ECG) signal, a photoplethysmogram (PPG) signal, an electromyography (EMG) signal, and the like, and various bio-signal sensors are being developed to measure the bio-signals in daily life. For example, the PPG sensor may estimate blood pressure of a human body by analyzing a pulse waveform which reflects a condition of the cardiovascular system and the like.

A general method of indirectly estimating blood pressure based on a bio-signal includes extracting various features relevant to blood pressure from a bio-signal, and estimating a blood pressure value based on the extracted features. Blood pressure may be changed by various mechanisms in daily life, and a changing tendency of systolic blood pressure (SBP) and diastolic blood pressure (DBP) may be different from each other in some cases. The related art methods of indirectly estimating blood pressure have a problem in that when decoupling occurs, in which the SBP and the DBP are changed with different change tendencies, the related art methods may not estimate SBP and DBP independently and accurately. For this reason, when using the methods of indirectly estimating blood pressure, in which it is difficult to independently estimate the SBP and the DBP, wrong blood pressure information may be provided to users.

SUMMARY

One or more exemplary embodiments provide an apparatus and a method for independently and accurately estimating systolic blood pressure (SBP) and diastolic blood pressure (DBP) in a non-invasive manner.

According to an aspect of an exemplary embodiment, there is provided a blood pressure estimating apparatus including: a sensor configured to obtain a bio-signal of an object; and a processor configured to extract a first cardiovascular feature and a second cardiovascular feature based on the bio-signal, and estimate blood pressure based on a first changing tendency of the first cardiovascular feature from a first reference level and a second changing tendency of the second cardiovascular feature from a second reference level, the first changing tendency and the second changing tendency being independent from each other.

The bio-signal may include at least one of a photoplethysmogram (PPG) signal, an electrocardiography (ECG) signal, an electromyography (EMG) signal, and a ballistocardiogram (BCG) signal.

The sensor may include a plurality of sensors configured to measure the bio-signal.

The apparatus may further include a communicator configured to receive the bio-signal from an external device.

The first cardiovascular feature may be a cardiac output and the second cardiovascular feature may be a total peripheral resistance.

The processor may extract the first cardiovascular feature and the second cardiovascular feature based on a characteristic point, the characteristic point including at least one of heart rate information, a shape of a waveform of the bio-signal, a time and an amplitude of a maximum point of the bio-signal, a time and an amplitude of a minimum point of the bio-signal, an area of the waveform of the bio-signal, and amplitude and time information of waveforms of constituent pulses constituting the bio-signal.

The processor may independently estimate systolic blood pressure (SBP) and diastolic blood pressure (DBP) based on the first changing tendency of the first cardiovascular feature and the second changing tendency of the second cardiovascular feature.

The processor may scale the first cardiovascular feature to a third cardiovascular feature and scale the second cardiovascular feature to a fourth cardiovascular feature. The processor may estimate the SBP based on the third cardiovascular feature, and estimate the DBP based on the fourth cardiovascular feature.

The first cardiovascular feature may be a cardiac output and the second cardiovascular feature may be a total peripheral resistance.

The processor may scale the cardiac output to a first cardiac output and a second cardiac output, and scale the total peripheral resistance to a first total peripheral resistance and a second total peripheral resistance. The processor may estimate the SBP by linearly combining the first cardiac output and the first total peripheral resistance, and estimate the DBP by linearly combining the second cardiac output and the second total peripheral resistance.

The processor may linearly combine the first cardiac output and the first total peripheral resistance after respectively applying a first weight and a second weight to the first cardiac output and the first total peripheral resistance; and linearly combine the second cardiac output and the second total peripheral resistance after respectively applying a third weight and a fourth weight to the second cardiac output and the second total peripheral resistance.

The processor may estimate the SBP by applying a predetermined first scaling factor to a result of a linear combination of the first cardiac output and the first total peripheral resistance; and estimate the DBP by applying a predetermined second scaling factor to a result of a linear combination of the second cardiac output and the second total peripheral resistance.

The processor may determine scaling degrees of the cardiac output and the total peripheral resistance based on the first changing tendency and the second changing tendency, respectively.

Based on the first changing tendency being a tendency of an increase, the processor may maintain or reduce a rate of an increase in the second cardiac output compared to a rate of an increase in the first cardiac output.

Based on the second changing tendency being a tendency of a decrease, the processor may maintain or increase a rate of a decrease in the second total peripheral resistance compared to a rate of a decrease in the first total peripheral resistance.

The apparatus may further include an output circuitry configured to output a blood pressure estimation result of the processor.

According to an aspect of another exemplary embodiment, there is provided a blood pressure estimating method including: obtaining a bio-signal of an object; extracting a first cardiovascular feature and a second cardiovascular feature based on the bio-signal; and estimating blood pressure based on a first changing tendency of the first cardiovascular feature from a first reference level and a second changing tendency of the second cardiovascular feature from a second reference level, the first changing tendency and the second changing tendency being independent from each other.

The bio-signal may include at least one of a photoplethysmogram (PPG) signal, an electrocardiography (ECG) signal, an electromyography (EMG) signal, and a ballistocardiogram (BCG) signal.

The first cardiovascular feature may be a cardiac output and the second cardiovascular feature may be a total peripheral resistance.

The extracting of the first cardiovascular feature and the second cardiovascular feature may include extracting the first cardiovascular feature and the second cardiovascular feature based on a characteristic point, the characteristic point including one or more of heart rate information, a shape of a waveform of the bio-signal, a time and an amplitude of a maximum point of the bio-signal, a time and an amplitude of a minimum point of the bio-signal, an area of the waveform of the bio-signal, an elapsed time of the bio-signal, amplitude and time information of a waveform of a constituent pulse constituting the bio-signal, and an internally dividing point between two or more characteristic points.

The estimating the blood pressure may include independently estimating systolic blood pressure (SBP) and diastolic blood pressure (DBP) based on the first changing tendency of the first cardiovascular feature and the second changing tendency of the second cardiovascular feature.

The method may further include scaling the cardiac output to a first cardiac output and a second cardiac output, and scaling the total peripheral resistance to a first total peripheral resistance and a second total peripheral resistance. The estimating the blood pressure may include estimating the SBP by linearly combining the first cardiac output and the first total peripheral resistance, and estimating the DBP by linearly combining the second cardiac output and the second total peripheral resistance.

The scaling the cardiac output and the total peripheral resistance may include determining scaling degrees of the cardiac output and the total peripheral resistance based on the first changing tendency and the second changing tendency, respectively.

In response to the first changing tendency being a tendency of an increase, the scaling may include maintaining or reducing a rate of an increase in the second cardiac output compared to a rate of an increase in the first cardiac output.

In response to the second changing tendency being a tendency of a decrease, the scaling may include maintaining or increasing a rate of a decrease in the second total peripheral resistance compared to a rate of a decrease in the first total peripheral resistance.

The method may further include outputting a blood pressure estimation result.

According to an aspect of another exemplary embodiment, there is provided a wearable device including: a main body worn on an object; a strap connected at a first end and a second end of the main body, and configured to be wrapped around the object to secure the main body to the object; a sensor mounted in the main body and configured to measure a bio-signal from the object; and a processor configured to extract a first cardiovascular feature and a second cardiovascular feature based on the bio-signal, and estimate blood pressure based on a first changing tendency of the first cardiovascular feature from a first reference level and a second changing tendency of the second cardiovascular feature from a second reference level, the first changing tendency and the second changing tendency being independent from each other.

The sensor may include at least one of a photoplethysmogram (PPG) sensor, an electrocardiography (ECG) sensor, an electromyography (EMG) sensor, and a ballistocardiogram (BCG) sensor.

The first cardiovascular feature may be a cardiac output and the second cardiovascular feature may be a total peripheral resistance.

The processor may independently estimate systolic blood pressure (SBP) and diastolic blood pressure (DBP) based on the first changing tendency of the first cardiovascular feature and the second changing tendency of the second cardiovascular feature.

The processor may scale the first cardiovascular feature to a third cardiovascular feature and scale the second cardiovascular feature to a fourth cardiovascular feature, and estimate the SBP based on the third cardiovascular feature and the DBP based on the fourth cardiovascular feature.

The wearable device may further include a display configured to output a blood pressure estimation result of the processor.

The wearable device may further include a communicator configured to transmit a result of estimating the blood pressure to an external device.

According to an aspect of another exemplary embodiment, there is provided a wearable device configured to be worn on an object and estimate blood pressure of the object, the wearable device including: a sensor configured to obtain a bio-signal from the object; and a processor configured to extract a first cardiovascular feature and a second cardiovascular feature based on the bio-signal, determine different first scaling degrees of the first cardiovascular feature and the second cardiovascular feature for estimating the systolic blood pressure (SBP), determine different second scaling degrees of the second cardiovascular feature for estimating diastolic blood pressure (DBP), and estimate the SBP and the DBP based on linear combinations of first cardiovascular features applied with the first scaling degrees and second cardiovascular features applied with the second scaling degrees, respectively, wherein the first scaling degrees and the second scaling degrees of the first cardiovascular feature and the second cardiovascular feature for estimating the SBP and the DBP are independently determined based on changing tendencies of the first cardiovascular feature and the second cardiovascular.

BRIEF DESCRIPTION OF THE DRAWINGS

The above and/or other aspects will become apparent and more readily appreciated from the following description of the exemplary embodiments, taken in conjunction with the accompanying drawings, in which:

FIGS. 5A to 5D are diagrams explaining examples of extracting and scaling of cardiovascular features;

FIG. 6 is a flowchart illustrating a blood pressure estimating method according to an exemplary embodiment;

DETAILED DESCRIPTION

Figure 1:
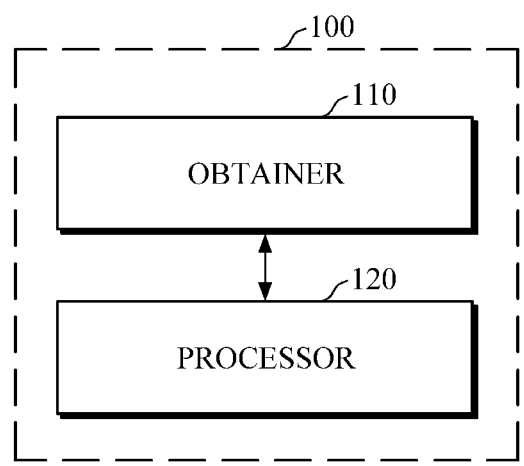
FIG. 1 is a block diagram illustrating a blood pressure estimating apparatus according to an exemplary embodiment.

Details of exemplary embodiments are included in the following detailed description and drawings. Aspects and features of the disclosure, and a method of achieving the same will be more clearly understood from the following embodiments described in detail with reference to the accompanying drawings. Throughout the drawings and the detailed description, unless otherwise described, like reference numerals will be understood to refer to like elements, features, and structures. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

As used herein, the term "and/or" includes any and all combinations of one or more of the associated listed items. Similarly, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, exemplary embodiments of a blood pressure estimating apparatus and blood pressure estimating method will be described in detail with reference to the accompanying drawings.

FIG. 1 is a block diagram illustrating a blood pressure estimating apparatus according to an exemplary embodiment.

The blood pressure estimating apparatus 100 may be embedded in a terminal, such as a smartphone, a tablet personal computer (PC), a desktop computer, a laptop computer, and the like, or may be manufactured as an independent hardware device. In this case, the independent hardware device may be a wearable device that may be worn on the wrist, examples thereof including a wristwatch-type wearable device, a bracelet-type wearable device, a wristband-type wearable device, a ring-type wearable device, a glasses-type wearable device, a hairband-type wearable device, or the like, but the hardware device is not limited thereto.

Referring to FIG. 1, the blood pressure estimating apparatus 100 includes an obtainer (or sensor) 110 and a processor 120.

The obtainer 110 may include one or more sensors, through which the obtainer 110 may measure various bio-signals from an object. In this case, the one or more sensors may be a photoplethysmogram (PPG) sensor, an electrocardiography (ECG) sensor, an electromyography (EMG) sensor, a ballistocardiogram (BCG), and the like, but the sensors are not limited thereto.

The processor 120 may measure blood pressure based on the bio-signals measured by the obtainer 110. Upon receiving the bio-signals from the obtainer 110, the processor 120 may extract cardiovascular features, which affect blood pressure, from the bio-signals. In this case, the cardiovascular features may include a cardiac output (CO), a total peripheral resistance (TPR), and the like, but are not limited thereto.

Upon extracting the cardiovascular features, the processor 120 may identify a changing tendency (or changing pattern) of the extracted cardiovascular feature compared to reference cardiovascular feature (or reference level of the cardiovascular features), and may estimate blood pressure by considering the changing tendency of the cardiovascular feature. In this case, the processor 120 may independently estimate systolic blood pressure (SBP) and diastolic blood pressure (DBP). The reference level of the cardiovascular feature may be a level of the cardiovascular feature at a stable stage. Also, the changing tendency of the cardiovascular feature refers to a tendency in a change of the value of the cardiovascular feature over time, compared to the reference level of the cardiovascular feature.

For example, by considering the changing tendency of each of the cardiovascular features, the processor 120 may scale each of the cardiovascular features to a cardiovascular feature for SBP and a cardiovascular feature for DBP, and may independently estimate the SBP and the DBP by using the scaled cardiovascular feature for the SBP and the scaled cardiovascular feature for the DBP. For example, upon applying a weight to each of the scaled cardiovascular features for the SBP and for the DBP, the processor 120 may estimate the SBP and the DBP based on a combination of the scaled cardiovascular features. For example, the processor 120 may linearly combine the scaled cardiovascular features and may estimate the SBP and the DBP based on a result of the linear combination. In this case, the processor 120 may apply a scaling factor, used for adjusting scaling of the entire cardiovascular features, to the result of the linear combination, and may estimate the SBP and the DBP by using the result.

Figure 2:
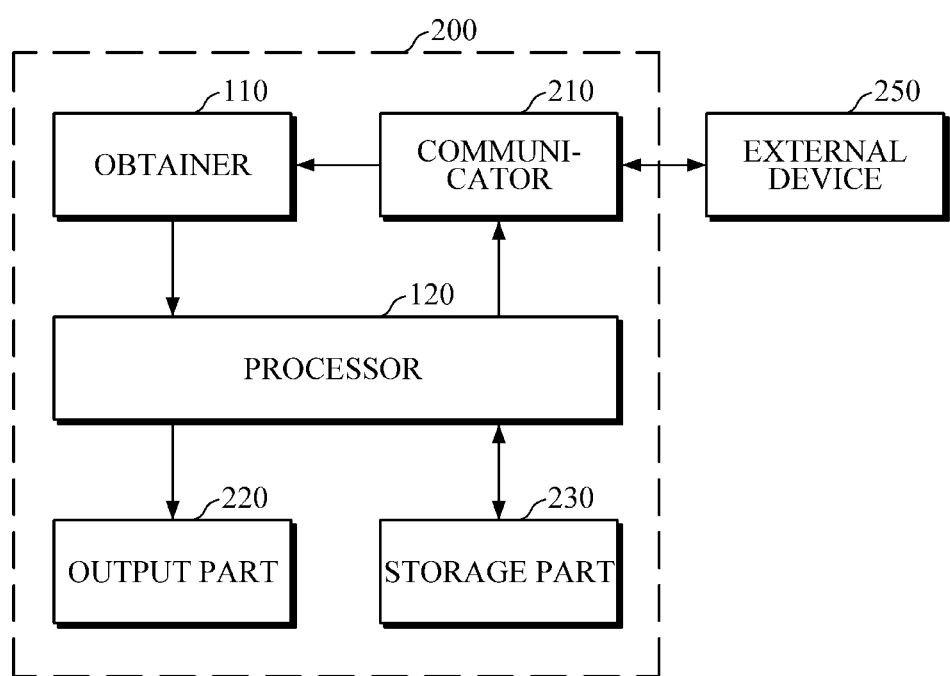
FIG. 2 is a block diagram illustrating a blood pressure estimating apparatus according to another exemplary embodiment.

FIG. 2 is a block diagram illustrating a blood pressure estimating apparatus according to another exemplary embodiment.

Referring to FIG. 2, the blood pressure estimating apparatus 200 includes an obtainer (or sensor) 110, a processor 120, a communicator 210, an output part 220, and a storage part 230. The obtainer 110 and the processor 120 are similar to or same as those described above with reference to FIG. 1, and repetitive descriptions thereof are avoided. One or more of the elements shown in FIG. 2 may be implemented by one or more hardware circuitry.

The communicator 210 may communicate with an external device 250 under the control of the processor 120 and estimate blood pressure in cooperation with the external device 250. For example, the communicator 210 may receive bio-signals from the external device 250 and may transmit the received bio-signals to the obtainer 110. In this case, the external device 250 may include a sensor to obtain bio-signals such as, for example but not limited to, photoplethysmogram (PPG), electrocardiography (ECG), electromyography (EMG), and ballistocardiogram (BCG). In this case, the obtainer 110 may include a minimum number of a sensor (e.g., only a minimum sensor such as a PPG sensor to obtain a PPG signal), thereby reducing the size of a main body of the blood pressure estimating apparatus 200.

Further, the communicator 210 may transmit a measurement result of bio-signals and/or an estimation result of blood pressure to the external device 250 under the control of the processor 120, so that the external device 250 may manage a blood pressure history or monitor a health state. In this case, examples of the external device 250 may include a smartphone, a tablet PC, a desktop computer, a laptop computer, a device of a medical institution, and the like, but the external device 250 is not limited thereto.

The communicator 210 may communicate with the external device by using one or more communication methods. Examples of the communication methods include, for example, BLUETOOTH™ communication, Bluetooth Low Energy (BLE) communication, Near Field Communication (NFC), WLAN communication, ZIGBEE™ communication, Infrared Data Association (IrDA) communication, Wi-Fi Direct (WFD) communication, Ultra-Wideband (UWB) communication, ANT+™ communication, Wi-Fi™ communication, Radio Frequency Identification (RFID) communication, 3G communication, 4G communication, 5G communication, and the like. However, this is merely exemplary and does not limit the disclosure.

The output part 220 may output additional information, such as the obtained bio-signals, the estimation result of blood pressure, a warning according to the estimation result of blood pressure, and the like. For example, the output part 220 may visually provide various types of information to a user through a display module (e.g., a display device). For example, in the case where an estimated blood pressure value falls outside a normal range when displaying the estimation result of blood pressure, the output part 220 may display warning information to a user by highlighting the blood pressure value in red, and the like. In another example, the output part 220 may provide various types of information to a user in a non-visual manner, such as through voice, vibration, tactility, or the like, using a speaker module (e.g., a speaker), a haptic module (e.g., a vibrator or a haptic motor), or the like.

For example, the output part 220 may notify a user of the SBP and the DBP through voice, vibration, and/or tactility. In the case where the estimated blood pressure value falls outside a normal range, the output part 220 may notify a user of the occurrence of abnormality in a health state through voice, vibration, and/or tactility. For example, the output part 220 may notify a user of the SBP and the DBP that fall within a normal range through voice and notify the user of the SBP and the DBP that fall outside the normal range through a vibration or tactility. However, this is merely exemplary and does not limit the disclosure.

The output part (or output circuitry) 220 may be implemented by one or more hardware circuitry.

The storage part 230 may store reference information, the obtained bio-signals, the estimation result of blood pressure, and the like. In this case, the reference information may include user information, such as a user's age, gender, health state, and the like, or an estimation model such as a blood pressure estimation equation.

In this case, the storage part 230 may include at least one storage medium of a flash memory type memory, a hard disk type memory, a multimedia card micro type memory, a card type memory (e.g., a secure digital (SD) memory, an extreme digital (XD) memory, etc.), a random access memory (RAM), a static random access memory (SRAM), a read only memory (ROM), an electrically erasable programmable read only Memory (EEPROM), a programmable read only memory (PROM), a magnetic memory, a magnetic disk, and an optical disk, and the like, but the storage medium is not limited thereto.

FIGS. 3A to 3D are diagrams explaining a correlation between a changing tendency of cardiovascular features and blood pressure.

Generally, mean blood pressure (MBP) is proportional to a cardiac output (CO) and a total peripheral resistance (TPR), as represented by the following Equation 1.

$$\Delta MBP = CO \times TPR \qquad [\text{Equation 1}]$$

Herein, ΔMBP denotes a difference in MBP between a left ventricle and a right atrium. Because MBP of the right atrium is generally in a range of 3 mmHg to 5 mmHg, MBP obtained by Equation 1 is similar to MBP of the left ventricle or MBP of an upper arm.

Generally, systolic blood pressure (SBP) and diastolic blood pressure (DBP) are values at points to the left and right in a waveform of the MBP and have a ratio to the value of the MBP in a range of 0.5 to 0.7. However, decoupling may occur when the SBP and the DBP do not follow a changing tendency of the MBP according to a change mechanism of blood pressure. Accordingly, in order to improve accuracy of estimating blood pressure, it is desirable to estimate blood pressure by considering effects caused by a change mechanism of blood pressure.

Figure 3A:
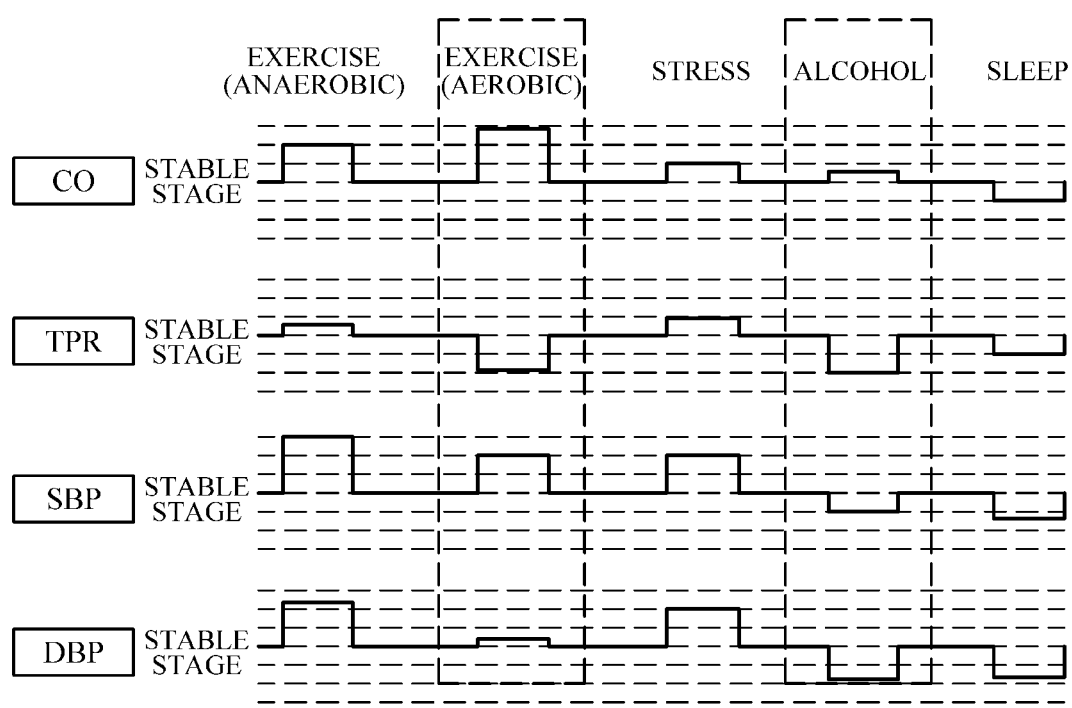
FIGS. 3A to 3D are diagrams explaining a correlation between a changing tendency of cardiovascular features and blood pressure.
Figure 3B:
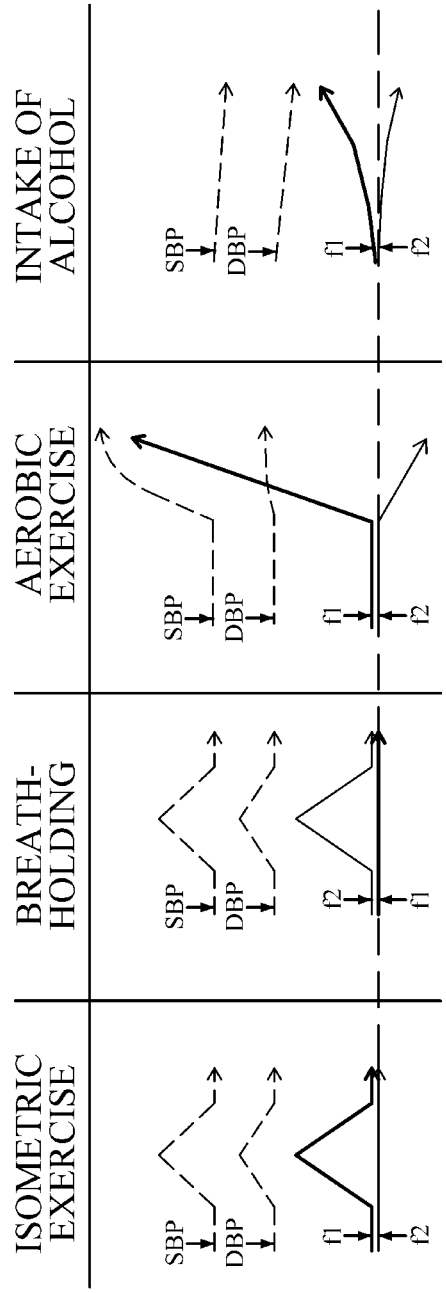

FIGS. 3A and 3B are diagram illustrating changing tendencies of SBP and DBP according to various change mechanisms of blood pressure.

Referring to FIGS. 3A and 3B, a changing tendency of the cardiac output (CO), the total peripheral resistance (TPR), the SBP, and the DBP may be estimated depending on various change mechanisms that affect the change in blood pressure.

For example, in the case where a change mechanism of blood pressure is anaerobic exercise or isometric exercise, the CO, the TPR, the SBP, and the DBP all show a tendency of an increase compared to a stable stage, and the tendency of the increase of the TPR is relatively insignificant. Accordingly, in the case where blood pressure is estimated by combining a CO feature f1 and a TPR feature f2, when a changing tendency shows that the CO feature f1 increases and the TPR feature f2 is maintained at substantially the same level (or has an insignificant changing tendency of an increase), the processor 120 may determine a state of anaerobic exercise or isometric exercise and estimate the SBP and the DBP as being proportional to a result of the combination of the CO feature f1 and the TPR feature f2.

In another example, in the case where a change mechanism of blood pressure is aerobic exercise, the CO and the SBP show a tendency of an increase compared to the stable stage, but the TPR and the DBP show tendency of a decrease. Accordingly, in the case where blood pressure is estimated by combining the CO feature f1 and the TPR feature f2, when a changing tendency is such that the CO feature f1 increases sharply while the TPR feature f2 decreases, the processor 120 may determine a state of aerobic exercise and estimate the SBP as increasing somewhat sharply and estimate the DBP as increasing very slightly.

In yet another example, in the case where a changing mechanism of blood pressure is alcohol, the CO shows a tendency of an increase compared to a stable stage, but all of the TPR, the SBP, and the DBP show a tendency of a decrease. Accordingly, in the case where blood pressure is estimated by combining the CO feature f1 and the TPR feature f2, when a degree of increase in the CO feature f1 is greater than a degree of decrease in the TPR feature f2, the SBP and the DBP may show a tendency of a decrease even when a result of the combination of the CO feature f1 and the TPR feature f2 shows a tendency of an increase. In this case, a degree of decrease in the DBP may be relatively greater than the SBP.

In still another example, in the case where a changing mechanism of blood pressure is breath-holding, and blood pressure is estimated by combining the CO feature f1 and the TPR feature f2, when the TPR feature f2 increases and CO feature f1 is maintained at the same level, both the SBP and the DBP are proportional to the result of the combination.

Figure 3C:
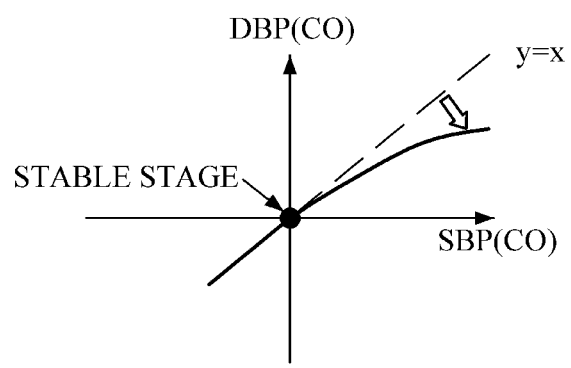
Figure 3D:
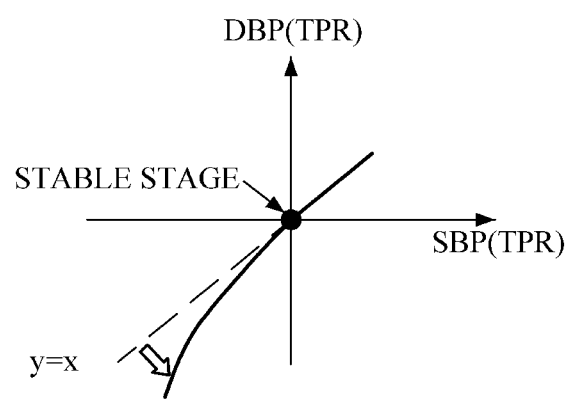

FIG. 3C is a diagram illustrating a changing tendency of SBP and DBP according to a change in CO, and FIG. 3D is a diagram illustrating a changing tendency of SBP and DBP according to a change in TPR.

Referring to FIG. 3C, when the CO increases or decreases, both the SBP and the DBP show a changing tendency of an increase or a decrease. When the CO decreases compared to a stable stage, both the SBP and the DBP show the same changing tendency of a decrease. However, when the CO gradually increases compared to the stable stage, changing tendencies of the SBP and the DBP are such that a degree of increase in the DBP becomes gradually smaller than a degree of increase in SBP. That is, as the CO (x axis) gradually increases, a degree of increase in the DBP (y axis) becomes gradually smaller; and as the CO (y axis) gradually increases, a degree of increase in the SBP (x axis) becomes gradually greater.

Referring to FIG. 3D, when the TPR increases or decreases, both the SBP and the DBP show a changing tendency of an increase or a decrease. When the TPR increases compared to the stable stage, both the SBP and the DBP show the same changing tendency of an increase. However, when the TPR gradually decreases compared to the stable stage, changing tendencies of the SBP and the DBP are such that a degree of decrease in the DBP becomes gradually greater than a degree of decrease in the SBP. That is, a changing tendency shows that as the CO (x axis) gradually decreases, a degree of decrease in the DBP (y axis) becomes gradually greater, and as the CO (y axis) gradually decreases, a degree of decrease in the SBP (x axis) becomes gradually smaller.

As described above, depending on the changing mechanisms of cardiovascular features, such as the CO, the TPR, and the like, and the SBP and the DBP show various changing tendencies. Particularly, the SBP is sensitive to a change in the CO, and the DBP is more sensitive to a change in the TPR. Accordingly, according to the exemplary embodiment, accuracy of estimating blood pressure may be improved by extracting cardiovascular features, such as the CO and/or TPR, from various bio-signals, by identifying a changing tendency by comparing the extracted cardiovascular features with reference levels of the cardiovascular features shown at a stable stage, and by independently estimating the SBP and the DBP by considering a changing tendency of the cardiovascular features.

Figure 4:
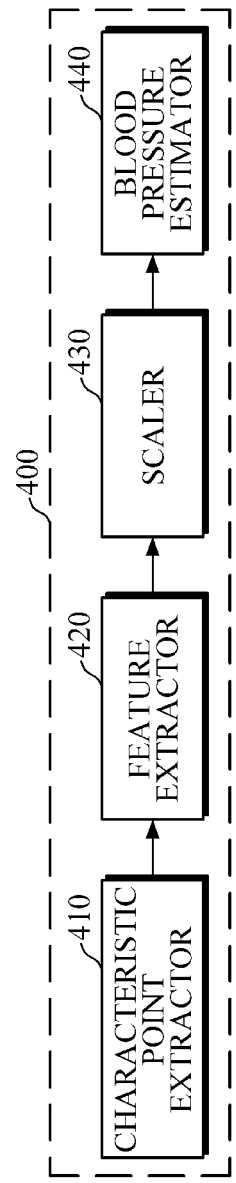
FIG. 4 is a block diagram illustrating a configuration of a processor in a blood pressure estimating apparatus according to an exemplary embodiment.

FIG. 4 is a block diagram illustrating a configuration of a processor in a blood pressure estimating apparatus according to an exemplary embodiment. FIGS. 5A to 5D are diagrams explaining examples of extracting and scaling of cardiovascular features.

By referring to FIGS. 4 to 5D, exemplary embodiments in which a processor 400 estimates blood pressure based on bio-signals will be described below. The processor 400 may be applied to the processor 100 or the processor 120 in the exemplary embodiments of FIGS. 1 and 2.

Referring to FIG. 4, the processor 400 includes a characteristic point extractor 410, a feature extractor 420, a scaler 430, and a blood pressure estimator 440.

The characteristic point extractor 410 may extract characteristic points for estimating blood pressure from various bio-signals. In this case, the characteristic points may include one or more of heart rate information, a shape of a bio-signal waveform, a time and an amplitude of a maximum point of a bio-signal, a time and an amplitude of a minimum point of a bio-signal, an area of a bio-signal waveform, an elapsed time of a bio-signal, amplitude and time information of a waveform of a constituent pulse constituting a bio-signal, and an internally dividing point between two or more characteristic points, but the characteristic points are not limited thereto.

Figure 5A:
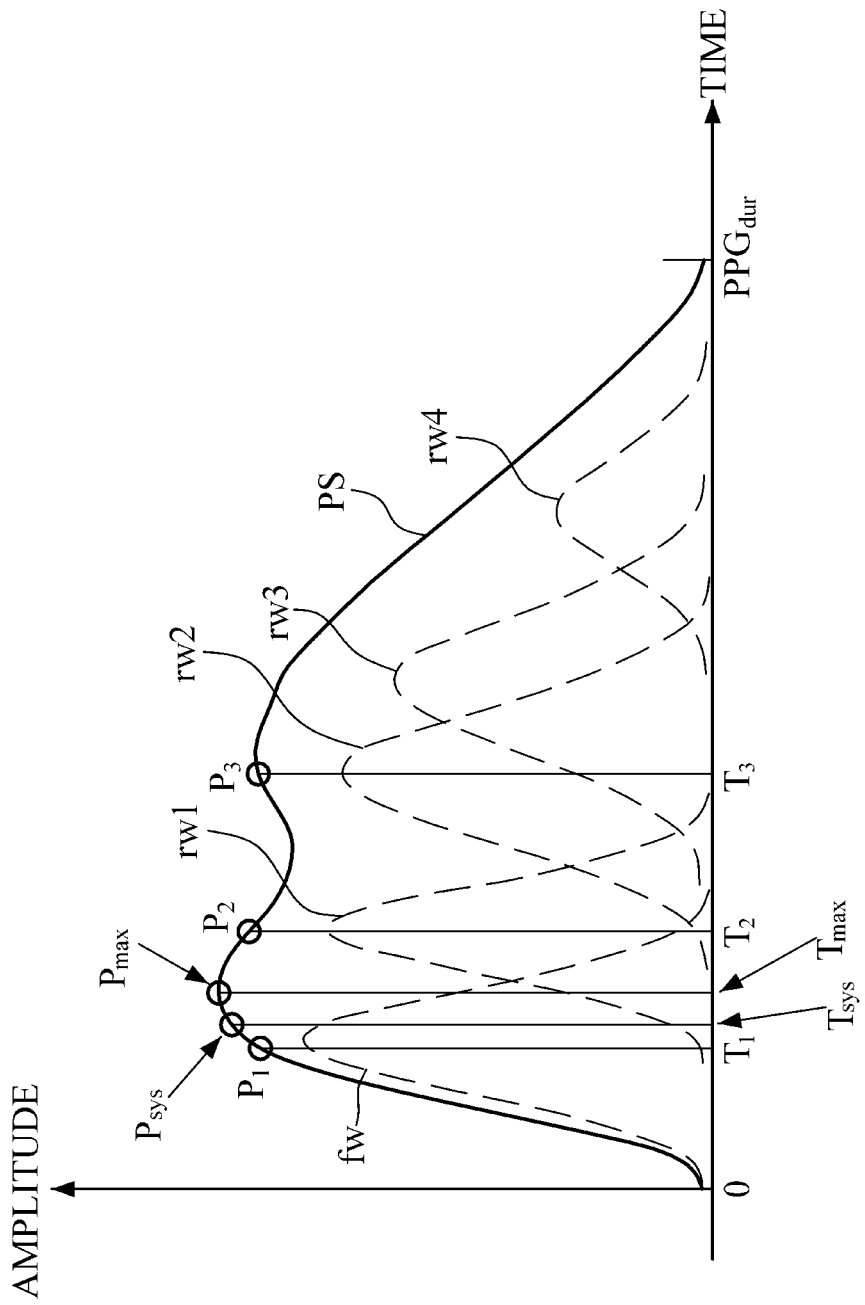

FIG. 5A is a diagram illustrating an example of a pulse wave signal among bio-signals obtained from an object.

Referring to FIG. 5A, an example where the characteristic point extractor 410 extracts characteristic points from the pulse wave signal will be described below.

Generally, the pulse wave signals are based on a superposition of propagation waves starting from the heart toward the distal end portions of the body and reflection waves returning back from the distal end portions. FIG. 5A illustrates an example where a waveform of a pulse wave signal PS obtained from an object is formed such that five constituent pulses, e.g., the propagation wave fw and the reflection waves rw1, rw2, rw3, and rw4, are superposed with each other.

The characteristic point extractor 410 may extract characteristic points from the pulse wave signal PS by analyzing the constituent pulse waveforms, for example, including a first constituent pulse waveform fw, a second constituent pulse waveform rw1, a third constituent pulse waveform rw2, a fourth constituent pulse waveform rw3, and a fifth constituent pulse waveform rw4. Generally, pulses up to the third constituent pulse are mainly used to estimate blood pressure. Pulses after the third constituent pulse rw2 may not be observed depending on individuals in some cases, and are difficult to be found due to noise or have a low correlation with estimation of blood pressure.

For example, the characteristic point extractor 410 may extract, as characteristic points, times $T_1$, $T_2$, and $T_3$, and amplitudes $P_1$, $P_2$, and $P_3$ of a maximum point of the first to the third constituent pulse waveforms fw, rw1, and rw2. In this case, upon obtaining the pulse wave signal PS, the characteristic point extractor 410 may secondarily differentiate the obtained pulse wave signal PS, and may extract the times $T_1$, $T_2$, and $T_3$, and the amplitudes $P_1$, $P_2$, and $P_3$ of the maximum point of the first to the third constituent pulse waveforms fw, rw1, and rw2 by using the secondary differential signal. For example, by detecting a local minimum point from the secondary differential signal, the characteristic point extractor 410 may extract the times $T_1$, $T_2$, and $T_3$ of the local minimum point of the first to the third constituent pulse waveforms fw, rw1, and rw2, and may extract amplitudes $P_1$, $P_2$, and $P_3$ corresponding to the times $T_1$, $T_2$, and $T_3$ from the pulse wave signal PS. Here, the local minimum point refers to a point having a form in which the corresponding signal is reduced and then increased again with respect to a specific point when some intervals of the secondary differential signal are observed. That is, the local minimum point may be extracted from a downward convex form of a pulse waveform.

In another example, the characteristic point extractor 410 may extract, as characteristic points, an amplitude $P_{max}$, at which an amplitude has a maximum value in a specific interval of the pulse wave signal PS, and a time a time $T_{max}$ corresponding to the amplitude $P_{max}$. In this case, the specific interval may refer to an interval between a starting point of the pulse wave signal PS and a point where a dicrotic notch (DN) appears, which indicates the SBP section.

In yet another example, the characteristic point extractor 410 may extract, as characteristic points, an elapsed time $PPG_{dur}$ indicating the entire measurement time of bio-signals, or an area $PPG_{area}$ of a bio-signal waveform that is measured. In this case, the area of the bio-signal waveform may refer to the entire area of a bio-signal waveform, or an area of a bio-signal waveform corresponding to a predetermined percentage (e.g., 70%) of the entire elapsed time $PPG_{dur}$ of the bio-signal measurement.

In still another example, the characteristic point extractor 410 may extract, as an additional characteristic point, an internally dividing point between the extracted two or more characteristic points. When an unstable waveform is generated in a pulse wave signal due to an abnormal environment such as motion noise, sleep, and the like, characteristic points may be extracted at wrong locations. The measurement of blood pressure may be supplemented by using the internally dividing point between the wrongly extracted characteristic points.

For example, upon extracting characteristic points ($T_1$, $P_1$) and ($T_{max}$, $P_{max}$) in the SBP section, the characteristic point extractor 410 may calculate characteristic points ($T_{sys}$, $P_{sys}$) of an internally dividing point between the extracted characteristic points ($T_1$, $P_1$) and ($T_{max}$, $P_{max}$). In this case, the characteristic point extractor 410 may apply a weight to the two characteristic points ($T_1$, $P_1$) and ($T_{max}$, $P_{max}$) and time values $T_1$ and $T_{max}$, may calculate a time $T_{sys}$ of the internally dividing point by using each of the time values to which the weight is applied, and may extract an amplitude $P_{sys}$ corresponding to the calculated time $T_{sys}$ of the internally dividing point. However, the internally dividing point is not limited thereto, and the characteristic point extractor 410 may further calculate an internally dividing point between the characteristic points ($T_1$, $P_1$) and ($T_2$, $P_2$) associated with the first and the second constituent pulse waveforms fw and $rw_1$ in the SBP section, and an internally dividing point between the characteristic points ($T_3$, $P_3$) and ($T_4$, $P_4$) associated with the third and the fourth constituent pulse waveforms $rw_2$ and $rw_3$ in the DBP section, and the like, by analyzing the waveform of the obtained bio-signal.

The feature extractor 420 may extract cardiovascular features, such as a cardiac output and/or a total peripheral resistance, by combining characteristic points extracted from various bio-signals.

FIG. 5B is a diagram illustrating examples of candidates for a cardiac output (CO) feature and candidates for a total peripheral resistance (TPR) feature.

For example, referring to FIG. 5B, the feature extractor 420 may extract, as a cardiac output feature, (1) a heart rate (HR) per minute, (2) an area PPGarea of a bio-signal; (3) a value P3/Pmax obtained by dividing an amplitude P3, extracted from the third constituent pulse waveform rw2, by a maximum amplitude Pmax in the SBP section; (4) a value P3/Psys obtained by dividing the amplitude P3 by an amplitude Psys of an internally dividing point; (5) a value Pmax/PPGarea obtained by dividing the maximum amplitude Pmax in the SBP section by the area PPGarea of a bio-signal waveform; (6) a reciprocal number of an elapsed time PPGdur of a bio-signal, and the like.

In another example, the feature extractor 420 may extract, as a total peripheral resistance feature, (1) a reciprocal number of a value obtained by subtracting the time T1 extracted from the first constituent pulse waveform fw from the time T3 extracted from the third constituent pulse waveform rw2; (2) a reciprocal number of a value obtained by subtracting the time Tsys of the internally dividing point (e.g., between the extracted characteristic points (T1, P1) and (Tmax, Pmax)) from the time T3 extracted from the third constituent pulse waveform rw2; (3) a reciprocal number of a value obtained by subtracting the time Tmax corresponding to the maximum amplitude Pmax in the SBP section from the time T3 extracted from the third constituent pulse waveform rw2; (4) a reciprocal number of a value obtained by subtracting the time T1 extracted from the first constituent pulse waveform fw from the time T2 extracted from the second constituent pulse waveform rw1; (5) a value obtained by dividing the amplitude P2 extracted from the second constituent pulse waveform rw1 by the amplitude P1 extracted from the first constituent pulse waveform fw; (6) a value obtained by dividing the amplitude P3 extracted from the third constituent pulse waveform rw2 by the maximum amplitude Pmax; (7) a value obtained by dividing the amplitude P3 extracted from the third constituent pulse waveform rw2 by the amplitude P1 extracted from the first constituent pulse waveform fw; and/or (8) the area PPGarea of a bio-signal. However, the extraction of the total peripheral resistance features is not limited thereto, and the features of the cardiac output or the total peripheral resistance may be extracted by a combination of various other characteristic points.

The scaler 430 may scale cardiovascular features, extracted by the feature extractor 420, to a first cardiovascular feature and a second cardiovascular feature by considering a changing tendency of the cardiovascular features. In this case, the first cardiovascular feature is a cardiovascular feature for estimating the SBP, and the second cardiovascular feature is a cardiovascular feature for estimating the DBP. The scaler 430 may determine a scaling degree of the first cardiovascular feature and the second cardiovascular feature according to a type (e.g., cardiac output or total peripheral resistance) and a changing tendency (e.g., increase or decrease) of the extracted cardiovascular features. In this case, the scaling degree may be pre-defined for each user through preprocessing. For example, the scaling degree may be customized for each user by considering attributes of the user or determined based on a prior experiment.

Figure 5C:
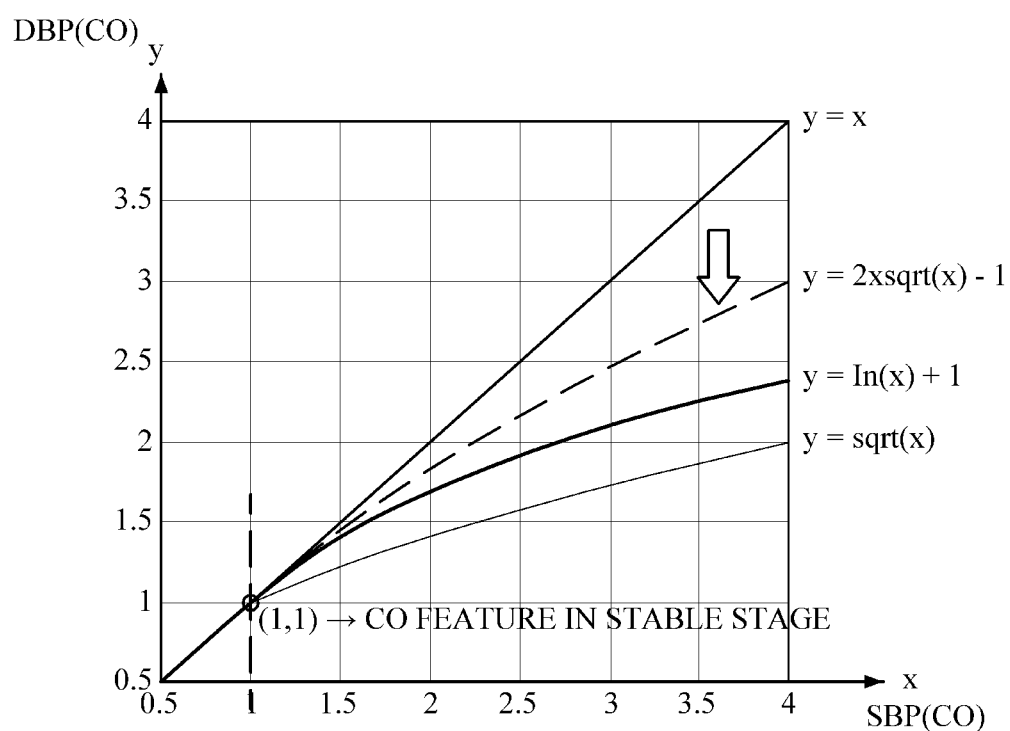

FIG. 5C illustrates an example of scaling the first cardiovascular feature for estimating the SBP and the second cardiovascular feature for estimating the DBP according to a type of cardiac output. As described above, in the case where the cardiac output is increased, the cardiac output feature has a greater effect on the SBP than on the DBP. Accordingly, referring to FIG. 5C, with respect to a section ($x>1$) in which the cardiac output is increased, in the case where a scaling degree of the first cardiovascular feature (e.g., first cardiac output) for estimating the SBP is defined by a formula of $y=x$, a scaling degree of the second cardiovascular feature (e.g., second cardiac output) for estimating the DBP may be defined by any one of $y=x$, $y=2\times\mathrm{sqrt}(x)-1$, $y=\ln(x)$, and $y=\mathrm{sqrt}(x)$, so that the scaling degree of the second cardiac output for estimating the DBP is equal to or less than a rate of increase in the first cardiac output for estimating the SBP.

Further, with respect to a section ($0 \leq x \leq 1$) in which the cardiac output is decreased, a scaling degree of the first cardiac output and a scaling degree of the second cardiac output may be defined by the same formula (e.g., $y=x$). However, the functional formulae are merely exemplary, and the scaling is not specifically limited thereto. In FIG. 5C, the x axis denotes a cardiac output before scaling, and the y axis denotes a cardiac output after scaling according to the scaling formula.

Also, a formula for determining the scaling degree of the first cardiovascular feature and a formula for determining the scaling degree of the second cardiovascular feature may be predetermined in the blood pressure estimating apparatus and may be later modified or adjusted if needed.

Figure 5D:
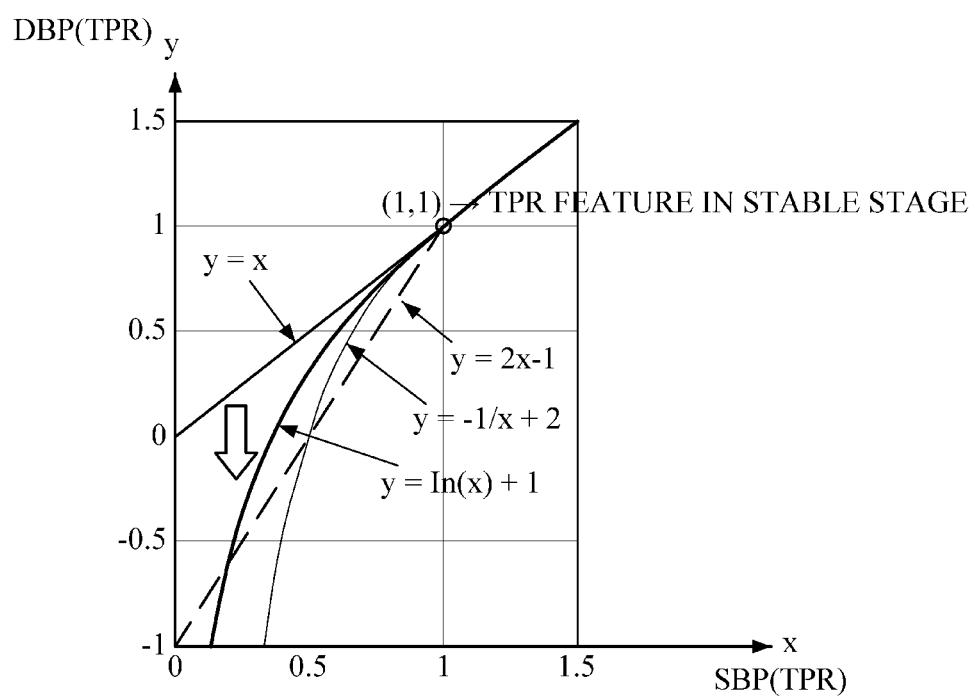

FIG. 5D illustrates an example of scaling the first cardiovascular feature for estimating the SBP and the second cardiovascular feature for estimating the DBP according to a type of total peripheral resistance. As described above, when the total peripheral resistance is deceased, the total peripheral resistance has a greater effect on the DBP than on the SBP. Accordingly, referring to FIG. 5D, with respect to a section ($0 \leq x \leq 1$) in which the total peripheral resistance is decreased, in the case where a scaling degree of the first cardiovascular feature (e.g., first total peripheral resistance) for estimating the SBP is defined by the formula of $y=x$, a scaling degree of the second cardiovascular feature (e.g., second total peripheral resistance) for estimating the DBP may be pre-defined by any one of $y=x$, $y=2\times x-1$, $y=-1/x+2$, and $y=\ln(x)+1$, so that the scaling degree of the second total peripheral resistance for estimating the DBP is equal to or greater than a rate of decrease in the first total peripheral resistance for estimating the SBP. Further, with respect to a section ($x>1$) in which the total peripheral resistance is increased, a scaling degree of the first total peripheral resistance and a scaling degree of the second total peripheral resistance may be defined by the same formula (e.g., $y=x$). However, the functional formulas are merely exemplary, and the calculation is not specifically limited thereto. In addition, in FIG. 5D, the x axis denotes a total peripheral resistance before scaling, and the y axis denotes a total peripheral resistance after scaling according to the scaling formula.

In the case where the cardiovascular features are scaled by the scaler 430 to a first cardiovascular feature and a second cardiovascular feature, the blood pressure estimator 440 may independently estimate SBP and DBP by applying the first cardiovascular feature and the second cardiovascular feature to an SBP estimation model and a DBP estimation model respectively. For example, the SBP estimation model and the DBP estimation model may be functional formulas represented by the following Equations 2 to 4, but are not limited thereto.

$$\mathrm{SBP}_{est} = A_{CO\_SBP} \times F_{CO\_SBP} + A_{TPR\_SBP} \times F_{TPR\_SBP} + B_{SBP} \quad \text{[Equation 2]}$$

$$\mathrm{DBP}_{est} = A_{CO\_DBP} \times F_{CO\_DBP} + A_{TPR\_DBP} \times F_{TPR\_DBP} + B_{DBP}$$

Equation 2 represents a functional formula as an example of a blood pressure estimation model. Herein, $\mathrm{SBP}_{est}$ denotes an SBP estimate, $A_{CO\_SBP}$ denotes a weight to be applied to the first cardiac output for SBP, $F_{CO\_SBP}$ denotes the scaled first cardiac output, $A_{TPR\_SBP}$ denotes a weight to be applied to the first total peripheral resistance for SBP and $F_{TPR\_SBP}$ denotes the scaled first total peripheral resistance, and $B_{SBP}$ denotes an SBP offset value. Further, $\mathrm{DBP}_{est}$ denotes an DBP estimate, $A_{CO\_DBP}$ denotes a weight to be applied to the second cardiac output for DBP, $F_{CO\_DBP}$ denotes the scaled second cardiac output, $A_{TPR\_DBP}$ denotes a weight to be applied to the second total peripheral resistance for DBP, $F_{TPR\_DBP}$ denotes the scaled second total peripheral resistance, and $B_{DBP}$ denotes an DBP offset value.

As represented by Equation 2, the blood pressure estimator 440 may estimate SBP by applying a weight value of the first cardiac output to the scaled first cardiac output and applying a weight value of the second cardiac output to the scaled first total peripheral resistance.

$$\mathrm{SBP}_{est} = \rho_{SBP} \times \{A_{CO\_SBP} \times F_{CO\_SBP} + A_{TPR\_SBP} \times F_{TPR\_SBP}\} + B_{SBP} \quad \text{[Equation 3]}$$

$$\mathrm{DBP}_{est} = \rho_{DBP} \times \{A_{CO\_DBP} \times F_{CO\_DBP} + A_{TPR\_DBP} \times F_{TPR\_DBP}\} + B_{DBP}$$

Equation 3 represents a functional formula as another example of a blood pressure estimation model, wherein $\rho_{SBP}$ denotes a scaling factor for SBP to adjust the entire scaling of the cardiovascular features, and $\rho_{DBP}$ denotes a scaling factor for DBP to adjust the entire scaling of the cardiovascular features.

$$\mathrm{SBP}_{est} = A_{SBP} \times F_{CO\_SBP} \times F_{TPR\_SBP} + B_{SBP} \quad \text{[Equation 4]}$$

$$\mathrm{DBP}_{est} = A_{DBP} \times F_{CO\_DBP} \times F_{TPR\_DBP} + B_{DBP}$$

Equation 4 represents a functional formula as yet another example of a blood pressure estimation model, wherein $A_{SBP}$ denotes a coefficient of SBP and $A_{DBP}$ denotes a coefficient of DBP.

FIG. 6 is a flowchart illustrating a blood pressure estimating method according to an exemplary embodiment.

The blood pressure estimating method of FIG. 6 is an example of the blood pressure estimating method according to one or more exemplary embodiments of FIG. 1 and FIG. 2, which have been described above in detail. Repetitive descriptions thereof are avoided.

The blood pressure estimating apparatus according to an exemplary embodiment may receive a request for estimating blood pressure in 610. The blood pressure estimating apparatus according to an exemplary embodiment may provide an interface for a user, and may receive the request for estimating blood pressure which is input by a user through the interface. Alternatively, the blood pressure estimating apparatus according to an exemplary embodiment may be connected to an external device through communication and may receive the request for estimating blood pressure from the external device. In this case, the external device may be a smartphone, a tablet PC, or the like which are carried by a user, and the user may control the operation of the blood pressure estimating apparatus by using a device having excellent or better interface performance or computing performance.

Then, in order to estimate blood pressure, the blood pressure estimating apparatus according to an exemplary embodiment may control a sensor mounted therein to obtain a bio-signal from an object or may receive a bio-signal from an external sensor in 620. In this case, the sensor mounted in the blood pressure estimating apparatus and the external sensor may obtain various bio-signals, such as a PPG signal, an ECG signal, an EMG signal, a BCG signal, and the like from various parts (e.g., wrist, chest, finger, etc.) of an object.

Subsequently, the blood pressure estimating apparatus according to an exemplary embodiment may extract characteristic points by analyzing the obtained bio-signal in 630. In this case, the characteristic points may include heart rate information, a shape of a bio-signal waveform, a time and an amplitude of a maximum point of a bio-signal, a time and an amplitude of a minimum point of a bio-signal, an area of a bio-signal waveform, an elapsed time of a bio-signal, amplitude and time information of a waveform of a constituent pulse constituting a bio-signal, and an internally dividing point between two or more characteristic points, and the like.

Next, the blood pressure estimating apparatus according to an exemplary embodiment may extract cardiovascular features based on the extracted characteristic points in 640. In this case, the cardiovascular features may include a cardiac output feature and a total peripheral resistance feature. For example, the blood pressure estimating apparatus may extract the cardiovascular features by using the extracted characteristic points as they are or by combining two or more characteristic points, as illustrated in FIG. 5B.

Then, the blood pressure estimating apparatus according to an exemplary embodiment may scale the extracted cardiovascular features to a first cardiovascular feature for estimating SBP in 650. In this case, by considering a correlation between SBP and a changing tendency of each of the cardiac output feature and the total peripheral resistance feature, and based on a pre-defined scaling degree, the blood pressure estimating apparatus may scale the cardiovascular features to a first cardiac output feature and a first total peripheral resistance feature.

In addition, the blood pressure estimating apparatus according to an exemplary embodiment may scale the extracted cardiovascular features to a second cardiovascular feature for estimating DBP in 660. In this case, by considering a correlation between DBP and a changing tendency of each of the cardiac output feature and the total peripheral resistance feature, and based on a pre-defined scaling degree, the blood pressure estimating apparatus may scale the cardiovascular features to a second cardiac output feature and a second total peripheral resistance feature.

For example, when the cardiac output is increased, the cardiac output feature has a greater effect on SBP than on DBP, such that in the case where the cardiac output feature has a tendency of an increase, the blood pressure estimating apparatus according to an exemplary embodiment may scale the second cardiac output so that a rate of increase in the second cardiac output feature is equal to or less than that of the first cardiac output feature. Further, when the total peripheral resistance is decreased, the total peripheral resistance feature has a greater effect on DBP than on SBP, such that in the case where the total peripheral resistance feature has a tendency of a decrease, the blood pressure estimating apparatus may scale the second total peripheral resistance so that a rate of decrease in the second total peripheral resistance feature is equal to or greater than that of the first total peripheral resistance feature.

Then, the blood pressure estimating apparatus according to an exemplary embodiment may estimate SBP by using the first cardiovascular feature in 670, and may estimate DBP by using the second cardiovascular feature in 680. For example, the blood pressure estimating apparatus may independently estimate SBP and DBP by applying the first cardiovascular feature and the second cardiovascular feature to an SBP estimation model and a DBP estimation model as represented above by Equations 2 to 4.

Subsequently, the blood pressure estimating apparatus according to an exemplary embodiment may output the obtained bio-signal, an estimation result of blood pressure, and additional information such as a warning according to the estimation result of blood pressure, and the like, and may provide the blood pressure estimation information to a user in 690. For example, the blood pressure estimating apparatus may visually output the estimation result of blood pressure through a display module, and in the case where the estimated blood pressure value falls outside a normal range when displaying the estimation result of blood pressure, the blood pressure estimating apparatus may display warning information along with the estimation result by highlighting the estimation result in red, and the like. Alternatively, the blood pressure estimating apparatus may output the estimation result of blood pressure through voice using a speaker module, in which in the case where the estimated blood pressure value falls outside a normal range, the blood pressure estimating apparatus may notify a user through vibration or tactility that there is abnormality in a health state. However, these examples are merely for illustrative purposes and do not limit the disclosure.

Figure 7A:
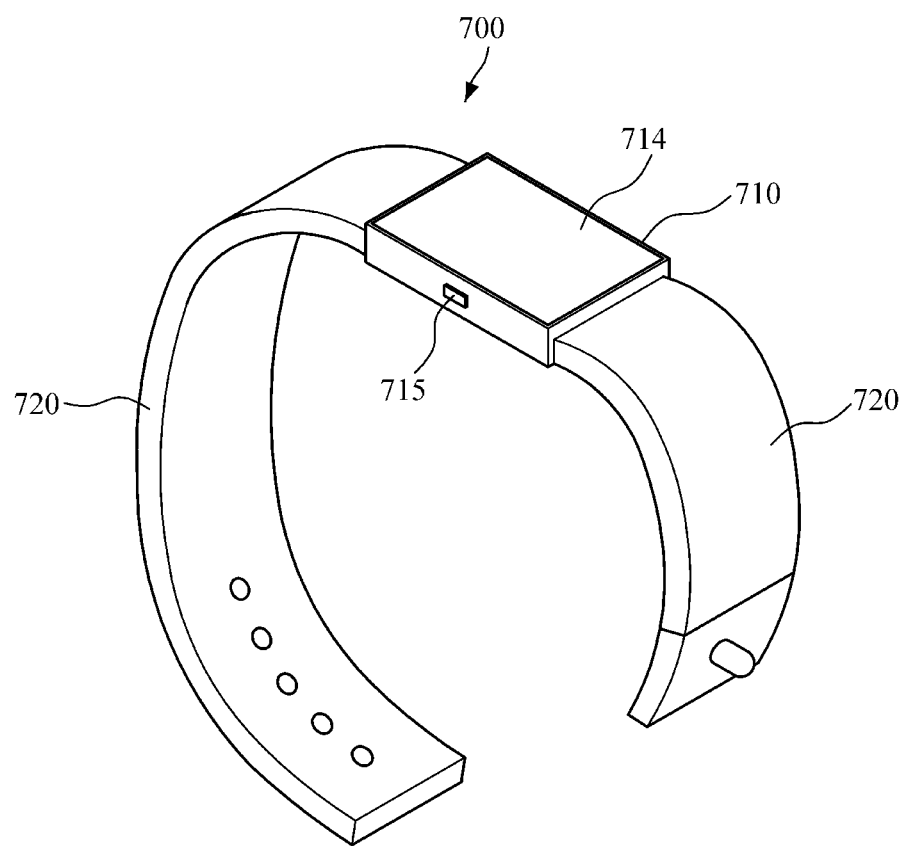
FIGS. 7A and 7B are diagrams explaining a wearable device according to an exemplary embodiment.
Figure 7B:
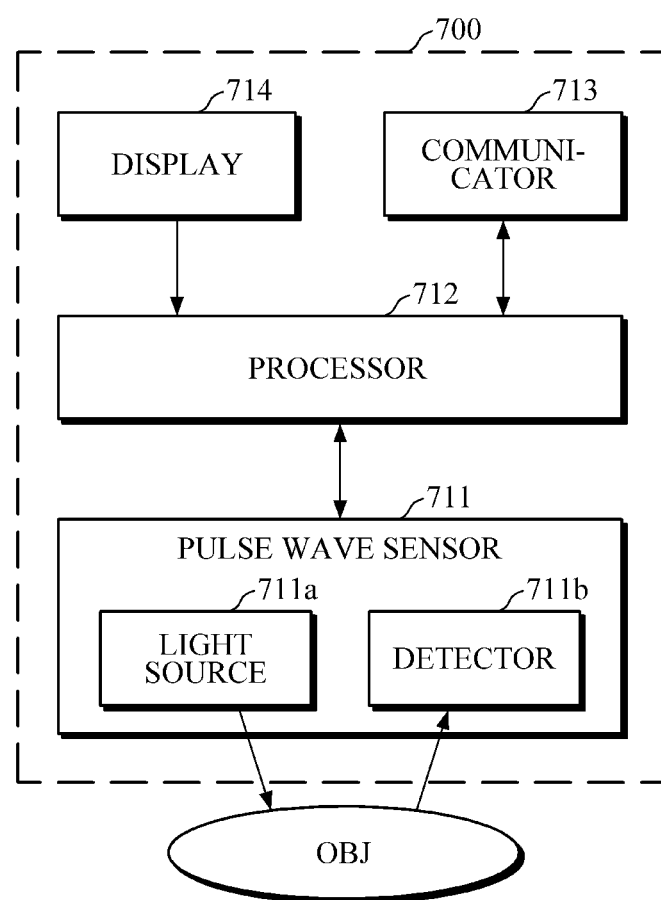

FIGS. 7A and 7B are diagrams explaining a wearable device according to an exemplary embodiment.

Various exemplary embodiments of the blood pressure estimating apparatus may be embedded in a smart watch or a smart band-type wearable device to be worn on the wrist as described in FIGS. 7A and 7B. However, this is merely exemplary for convenience of explanation, and the type of a wearable device is not specifically limited thereto.

Referring to FIGS. 7A and 7B, a wearable device 700 according to an exemplary embodiment includes a main body 710 and a strap 720.

The strap 720 may be flexible, and may be bent around a user's wrist or may be bent in a manner which allows the strap 720 to be detachable from the user's wrist. Alternatively, the strap 720 may be formed as a band that is not detachable. In this case, air may be injected into the strap 720 or an airbag may be included in the strap 720, so that the strap 720 may have elasticity cording to a change in pressure applied to the wrist, and the change in pressure of the wrist may be transmitted to the main body 710.

A battery, which supplies power to the wearable device 700, may be embedded in the main body 710 or the strap 720.

Further, the main body 710 may include one or more sensors to measure various bio-signals. For example, a pulse wave sensor 711 may be mounted at a rear surface of the main body 710 to be exposed to a portion that comes into contact with an object OBJ, e.g., a user's wrist. The pulse wave sensor 711 may include a light source 711a to emit light onto the object OBJ, and a detector 711*b* to measure a pulse wave signal by detecting light scattered or reflected from the object OBJ. In this case, the light source 711*a* may include, for example but not limited to, at least one of a light emitting diode (LED), a laser diode, and a fluorescent body, and may be formed in an array or two or more arrays. The light source formed in two or more arrays may emit light of different wavelengths. Further, the detector 711*b* may include, for example but not limited to, a photodiode, an image sensor, and the like, and may be formed in an array or two or arrays.

The main body 710 of the wearable device 700 may include a processor 712 for estimating blood pressure based on a bio-signal received from the pulse wave sensor 711 and/or an external sensor. In response to a user's request for estimating blood pressure, the processor 712 generates a control signal to control the pulse wave sensor 711, and depending on an embodiment, the processor 712 controls the communicator 713 to receive a bio-signal from the external sensor.

The communicator 713 may be mounted in the main body 710, and may communicate with an external device under the control of the processor 712 to transmit and receive information. For example, the communicator 713 may receive a bio-signal from an external sensor, e.g., an ECG sensor, an EMG sensor, a BCG sensor, and the like, which measures a bio-signal. Further, the communicator 713 may receive a request for estimating blood pressure from a mobile terminal of a user. In addition, the communicator 713 may also transmit extracted characteristic points or feature information to the external device to enable estimation of blood pressure. Moreover, the communicator 713 may transmit an estimation result of blood pressure to the external device to enable the estimation result to be displayed to a user, or to be used for various purposes such as management of a blood pressure history, disease research, and the like. Further, the communicator 713 may receive, from the external device, reference information such as a blood pressure estimation model or a scaling formula for each cardiovascular feature.

Once a bio-signal is received from the pulse wave sensor 711 and/or the external sensor, the processor 712 may extract characteristic points from the received bio-signal. For example, once a pulse wave signal is received, the processor 712 may analyze waveforms of constituent pulses constituting a pulse wave signal, and may extract, as characteristic points, a time and an amplitude of a maximum point of each constituent pulse waveform, a time and an amplitude at a point where an amplitude has a maximum value in an SBP section, an elapsed time of a pulse wave signal, an area of a waveform of a pulse wave signal, and the like, as described above.

Upon extracting the characteristic points, the processor 712 may extract cardiovascular features, such as a cardiac output feature and a total peripheral resistance feature, based on the extracted characteristic points as illustrated in FIG. 5B.

Further, the processor 712 may scale the cardiovascular features to a cardiovascular feature for SBP and a cardiovascular feature for DBP, and may independently estimate SBP and DBP by using the cardiovascular feature for SBP and the cardiovascular feature for DBP. In this case, a scaling degree of the cardiovascular feature for SBP and a scaling degree of the cardiovascular feature for DBP may be pre-defined by considering a correlation between a changing tendency of the cardiovascular features, e.g., the cardiac output feature and the total peripheral resistance feature, and SBP and DBP.

The processor 712 may store the estimation result of blood pressure, blood pressure history information, a bio-signal used for measuring blood pressure, the extracted characteristic points, the cardiovascular features before and after scaling, and the like in a storage device.

The wearable device 700 may further include a manipulator 715 and a display 714 which are mounted in the main body 710.

The manipulator 715 receives a control command of a user and transmits the received control command to the processor 712. The manipulator 715 may include a power button to turn on/off the wearable device 700.

Under the control of the processor 712, the display 714 may provide various types of information, associated with detected blood pressure, to a user. For example, the display 714 may display additional information, such as the detected blood pressure, alarm information, warning information, and the like, to a user by various visual/non-visual methods.

The exemplary embodiments of the disclosure can be implemented as a computer-readable code written on a computer readable recording medium. The computer-readable recording medium may be any type of recording device in which data is stored in a computer-readable manner.

Examples of the computer-readable recording medium include a read only memory (ROM), a random access memory (RAM), a compact-disk (CD)-ROM a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments to implement the exemplary embodiments of the disclosure can be easily deduced by one of ordinary skill in the art.

At least one of the components, elements, modules or units represented by a block as illustrated in the drawings may be embodied as various numbers of hardware, software and/or firmware structures that execute respective functions described above, according to an embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or be implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the embodiments may be implemented in algorithms that execute on one or more processors. Furthermore, the components, elements or units represented by a block or processing operations may employ any number of related art techniques for electronics configuration, signal processing and/or control, data processing and the like.

Although a few embodiments have been shown and described, it would be appreciated by those skilled in the art that changes may be made in exemplary embodiments without departing from the principles and spirit of the disclosure, the scope of which is defined in the claims and their equivalents.

What is claimed is:

1. A blood pressure estimating apparatus comprising:
at least one sensor configured to obtain a bio-signal of an object; and
a processor configured to:
extract a first cardiovascular feature and a second cardiovascular feature based on the bio-signal, and estimate blood pressure based on a first changing tendency of the first cardiovascular feature from a first reference level and a second changing tendency of the second cardiovascular feature from a second reference level, the first changing tendency and the second changing tendency being independent from each other,
wherein the processor is further configured to:
scale the first cardiovascular feature to a third cardiovascular feature and scale the second cardiovascular feature to a fourth cardiovascular feature; and
estimate systolic blood pressure (SBP) based on the third cardiovascular feature, and independently estimate diastolic blood pressure (DBP) based on the fourth cardiovascular feature, wherein scaling of the first cardiovascular feature and the second cardiovascular feature is such that, based on whether the first changing tendency is a tendency of an increase or a tendency of a decrease, a rate of an increase or a decrease in the fourth cardiovascular feature is different compared to a rate of an increase or a decrease in the third cardiovascular feature.

2. The apparatus of claim 1, wherein the bio-signal comprises at least one of a photoplethysmogram (PPG) signal, an electrocardiography (ECG) signal, an electromyography (EMG) signal, and a ballistocardiogram (BCG) signal.

3. The apparatus of claim 2, wherein the at least one sensor comprises a plurality of sensors configured to obtain the bio-signal.

4. The apparatus of claim 1, further comprising a communicator circuitry configured to receive the bio-signal from an external device.

5. The apparatus of claim 1, wherein the first cardiovascular feature is a cardiac output and the second cardiovascular feature is a total peripheral resistance.

6. The apparatus of claim 1, wherein the processor is further configured to extract at least one of the first cardiovascular feature and the second cardiovascular feature based on a characteristic point, the characteristic point comprising at least one of heart rate information, a shape of a waveform of the bio-signal, a time and an amplitude of a maximum point of the bio-signal, a time and an amplitude of a minimum point of the bio-signal, an area of the waveform of the bio-signal, and amplitude and time information of waveforms of constituent pulses constituting the bio-signal.

7. The apparatus of claim 1, wherein the first cardiovascular feature is a cardiac output and the second cardiovascular feature is a total peripheral resistance.

8. The apparatus of claim 7, wherein the processor is further configured to scale the cardiac output to a first cardiac output and a second cardiac output, and scale the total peripheral resistance to a first total peripheral resistance and a second total peripheral resistance, and
wherein the processor is further configured to estimate the SBP by linearly combining the first cardiac output and the first total peripheral resistance, and estimate the DBP by linearly combining the second cardiac output and the second total peripheral resistance.

9. The apparatus of claim 8, wherein the processor is further configured to:
linearly combine the first cardiac output and the first total peripheral resistance after respectively applying a first weight and a second weight to the first cardiac output and the first total peripheral resistance; and
linearly combine the second cardiac output and the second total peripheral resistance after respectively applying a third weight and a fourth weight to the second cardiac output and the second total peripheral resistance.

10. The apparatus of claim 8, wherein the processor is further configured to:
estimate the SBP by applying a predetermined first scaling factor to a result of a linear combination of the first cardiac output and the first total peripheral resistance; and
estimate the DBP by applying a predetermined second scaling factor to a result of a linear combination of the second cardiac output and the second total peripheral resistance.

11. The apparatus of claim 8, wherein the processor is further configured to determine scaling degrees of the cardiac output and the total peripheral resistance based on the first changing tendency and the second changing tendency, respectively.

12. The apparatus of claim 11, wherein based on the first changing tendency being the tendency of the increase, the processor is further configured to reduce a rate of an increase in the second cardiac output compared to a rate of an increase in the first cardiac output.

13. The apparatus of claim 11, wherein based on the second changing tendency being the tendency of the decrease, the processor is further configured to increase a rate of a decrease in the second total peripheral resistance compared to a rate of a decrease in the first total peripheral resistance.

14. The apparatus of claim 1, further comprising an output circuitry configured to output a blood pressure estimation result of the processor.

15. A blood pressure estimating method comprising:
obtaining a bio-signal of an object;
extracting a first cardiovascular feature and a second cardiovascular feature based on the bio-signal; and
estimating blood pressure based on a first changing tendency of the first cardiovascular feature from a first reference level and a second changing tendency of the second cardiovascular feature from a second reference level, the first changing tendency and the second changing tendency being independent from each other,
wherein the estimating comprises:
scaling the first cardiovascular feature to a third cardiovascular feature and scaling the second cardiovascular feature to a fourth cardiovascular feature; and
estimating systolic blood pressure (SBP) based on the third cardiovascular feature, and independently estimating diastolic blood pressure (DBP) based on the fourth cardiovascular feature, wherein scaling of the first cardiovascular feature and the second cardiovascular feature is such that, based on whether the first changing tendency is a tendency of an increase or a tendency of a decrease, a rate of an increase or a decrease in the fourth cardiovascular feature is different compared to a rate of an increase or a decrease in the third cardiovascular feature.

16. The method of claim 15, wherein the bio-signal comprises at least one of a photoplethysmogram (PPG) signal, an electrocardiography (ECG) signal, an electromyography (EMG) signal, and a ballistocardiogram (BCG) signal.

17. The method of claim 15, wherein the first cardiovascular feature is a cardiac output and the second cardiovascular feature is a total peripheral resistance.

18. The method of claim 15, wherein the extracting at least one of the first cardiovascular feature and the second cardiovascular feature comprises extracting the first cardiovascular feature and the second cardiovascular feature based on a characteristic point, the characteristic point comprising at least one of heart rate information, a shape of a waveform of the bio-signal, a time and an amplitude of a maximum point of the bio-signal, a time and an amplitude of a minimum point of the bio-signal, an area of the waveform of the bio-signal, an elapsed time of the bio-signal, amplitude and time information of a waveform of a constituent pulse constituting the bio-signal, and an internally dividing point between at least two characteristic points.

19. The method of claim 17, further comprising scaling the cardiac output to a first cardiac output and a second cardiac output, and scaling the total peripheral resistance to a first total peripheral resistance and a second total peripheral resistance, and
wherein the estimating the blood pressure comprises estimating the SBP by linearly combining the first cardiac output and the first total peripheral resistance, and estimating the DBP by linearly combining the second cardiac output and the second total peripheral resistance.

20. The method of claim 19, wherein the scaling the cardiac output and the total peripheral resistance comprises determining scaling degrees of the cardiac output and the total peripheral resistance based on the first changing tendency and the second changing tendency, respectively.

21. The method of claim 20, wherein based on the first changing tendency being the tendency of the increase, the scaling comprises maintaining or reducing a rate of an increase in the second cardiac output compared to a rate of an increase in the first cardiac output.

22. The method of claim 20, wherein based on the second changing tendency being the tendency of the decrease, the scaling comprises maintaining or increasing a rate of a decrease in the second total peripheral resistance compared to a rate of a decrease in the first total peripheral resistance.

23. The method of claim 15, further comprising outputting a blood pressure estimation result.

24. A wearable device comprising:
a main body worn on an object;
a strap connected at a first end and a second end of the main body, the strap being configured to be wrapped around the object to secure the main body to the object;
at least one sensor mounted in the main body and configured to obtain a bio-signal from the object; and
a processor configured to extract a first cardiovascular feature and a second cardiovascular feature based on the bio-signal, and estimate blood pressure based on a first changing tendency of the first cardiovascular feature from a first reference level and a second changing tendency of the second cardiovascular feature from a second reference level, the first changing tendency and the second changing tendency being independent from each other,
wherein the processor is further configured to:
scale the first cardiovascular feature to a third cardiovascular feature and scale the second cardiovascular feature to a fourth cardiovascular feature; and
estimate systolic blood pressure (SBP) based on the third cardiovascular feature, and independently estimate diastolic blood pressure (DBP) based on the fourth cardiovascular feature, wherein scaling of the first cardiovascular feature and the second cardiovascular feature is such that, based on whether the first changing tendency is a tendency of an increase or a tendency of a decrease, a rate of an increase or a decrease in the fourth cardiovascular feature is different compared to a rate of an increase or a decrease in the third cardiovascular feature.

25. The wearable device of claim 24, wherein the at least one sensor comprises at least one of a photoplethysmogram (PPG) sensor, an electrocardiography (ECG) sensor, an electromyography (EMG) sensor, and a ballistocardiogram (BCG) sensor.

26. The wearable device of claim 24, wherein the first cardiovascular feature is a cardiac output and the second cardiovascular feature is a total peripheral resistance.

27. The wearable device of claim 24, further comprising a display configured to output a blood pressure estimation result of the processor.

28. The wearable device of claim 24, further comprising a communicator circuitry configured to transmit a result of estimating the blood pressure to an external device.

* * * * *